US012778910B2

(12) United States Patent
Wärnheim et al.

(10) Patent No.: US 12,778,910 B2
(45) Date of Patent: Nov. 3, 2026

(54) TREATMENT REGIMEN FOR ONCHYOMYCOSIS USING ALLYLAMINE ANTIFUNGAL COMPOSITIONS

(71) Applicant: MOBERG PHARMA AB, Bromma (SE)

(72) Inventors: Torbjörn Wärnheim, Spånga (SE); Amir Tavakkol, Mountain Lakes, NJ (US)

(73) Assignee: MOBERG PHARMA AB, Bromma (SE)

( * ) Notice: Subject to any disclaimer, the term of this patent is extended or adjusted under 35 U.S.C. 154(b) by 0 days.

(21) Appl. No.: 19/418,539

(22) Filed: Dec. 12, 2025

(65) Prior Publication Data

US 2026/0102363 A1 Apr. 16, 2026

Related U.S. Application Data

(63) Continuation of application No. 18/256,446, filed as application No. PCT/GB2021/053195 on Dec. 7, 2021, now abandoned.

(60) Provisional application No. 63/122,588, filed on Dec. 8, 2020.

(51) Int. Cl.

| | |
|---|---|
| ***A61K 31/137*** | (2006.01) |
| ***A61K 9/00*** | (2006.01) |
| ***A61K 9/08*** | (2006.01) |
| ***A61K 47/10*** | (2017.01) |
| ***A61K 47/12*** | (2006.01) |
| ***A61K 47/14*** | (2017.01) |
| ***A61K 47/18*** | (2017.01) |
| ***A61P 31/10*** | (2006.01) |

(52) U.S. Cl.

CPC .......... *A61K 31/137* (2013.01); *A61K 9/0014* (2013.01); *A61K 9/08* (2013.01); *A61K 47/10* (2013.01); *A61K 47/12* (2013.01); *A61K 47/14* (2013.01); *A61K 47/18* (2013.01); *A61K 47/183* (2013.01); *A61P 31/10* (2018.01)

(58) Field of Classification Search

CPC ...... A61K 9/00; A61K 9/0002; A61K 9/0012; A61K 9/0087; A61K 9/06; A61K 9/08; A61K 9/10; A61K 38/68; A61K 31/137

See application file for complete search history.

(56) References Cited

U.S. PATENT DOCUMENTS

| | | | | |
|---|---|---|---|---|
| 7,820,720 | B2 | 10/2010 | Cevc et al. | |
| 2003/0235541 | A1 * | 12/2003 | Maibach | A61K 47/32 514/35 |
| 2004/0096410 | A1 | 5/2004 | Maley et al. | |
| 2008/0188568 | A1 | 8/2008 | Suvanprakorn et al. | |

FOREIGN PATENT DOCUMENTS

| | | | | |
|---|---|---|---|---|
| WO | 2006/103638 | A2 | 10/2006 | |
| WO | 2008/121709 | A1 | 10/2008 | |
| WO | 2010/010470 | A2 | 1/2010 | |
| WO | WO-2011014850 | A2 * | 2/2011 | A61K 9/0014 |
| WO | 2012/107565 | A1 | 8/2012 | |

OTHER PUBLICATIONS

International Search Report and Written Opinion for corresponding Application No. PCT/GB2021/053195 (mailedFeb. 23, 2022).

Elewski et al.,"Efficacy, Safety and Tolerability of Topical Terbinafine Nail Solutionin Patients with Mild-to-Moderate Toenail Onychomycosis: Results From Three Randomized Studies Using Double-Blind Vehicle-Controlled and Open-Label Active-Controlled Designs", J.Euro. Acad.Dermatol.Venereol. 27(3):287-294 (2011).

Blume-Peytavi et al.,"A Multicentre, Randomised, Parallel-Group, Double-Blind, Vehicle-Controlled and Open-Label, Active-Controlled Study (Versus Amorolfine 5%), to Evaluate the Efficacy and Safety of Terbinafine 10% Nail Lacquer in the Treatment of Onychomycosis", Mycoses. 65:392-401 (2021).

Gupta et al., "Onchomycosis: A Review," J. Euro. Acad. Dermatol. Venereol. 34(9):1972-1990 (2020).

Sun et al., "Nail Penetration—Focus on Topical Delivery of Antifungal Drugs for Onychomycosis Treatment," Topical Absorption of Dermatological Products, Eds. Bronaugh and Maibach, Marcel Dekker, Inc., New York, 2002, Chapter 30, pp. 437-455.

Press Release: "Moberg Pharma Meets Primary Endpoint for MOB-015 in a Phase 3 Study for the Treatment of Onychomycosis," (Dec. 9, 2019).

Press Release: "Moberg Pharma Comments on the Results of the North American Phase 3 Study with MOB-015," (Dec. 12, 2019).

Press Release: "Expert Evaluation Clarifies Phase 3 Results and Provides Strong Support for MOB-015," (Jan. 22, 2022).

Press Release: "Moberg Pharma Meets Primary Endpoint in the European Phase 3 Study," (Jun. 25, 2020).

Faergemann et al., "Early and Visible Improvements After Application of K101 in the Appearance of Nails Discoloured and Deformed by Onychomycosis," Journal of Cosmetics, Dermatological Sciences and Applications 1:59-63 (2011).

Piraccini et al., "Early Visible Improvements During K101-03 Treatment: An Open-Label Multicenter Clinical Investigation in Patients with Onychomycosis and/or Nail Psoriasis," Dermatology 233(2-3):178-183 (2017).

(Continued)

*Primary Examiner* — Micah Paul Young

(74) *Attorney, Agent, or Firm* — Troutman Pepper Locke LLP (Rochester)

(57) ABSTRACT

There is provided a method of treating onychomycosis of the nail, comprising topical application of a pharmaceutical composition comprising an antifungal allylamine compound and a non-aqueous solvent system, which method comprises a loading phase, during which the pharmaceutical composition is administered at least three times a week, followed by a maintenance phase, during which the pharmaceutical composition is administered no more than two times per week. There are further provided pharmaceutical compositions suitable for topical application to the nail comprising an antifungal allylamine compound, an organic acid component and a diol component, as defined herein, and their use in methods of treating onychomycosis.

8 Claims, 1 Drawing Sheet

(56) References Cited

OTHER PUBLICATIONS

Moberg Pharma, Interim Report Oct.-Dec. 2019.
Gupta et al., "Efficacy and Safety of Topical Terbinafine 10% Solution (MOB-015) in the Treatment of Mild to Moderate Distal Subungual Onychomycosis: A Randomized, Multicenter, Double-Blind, Vehicle-Controlled Phase 3 Study," J. Am. Acad. Dermatol. 85:95-104 (2021).
Moberg Pharma, Market Update, Nov. 25, 2020.
Moberg Pharma. Prospectus; Invitation to Subscribe for Units Consisting of Shares and Warrants in Moberg Pharma AB (publ), Dec. 3, 2020.

* cited by examiner

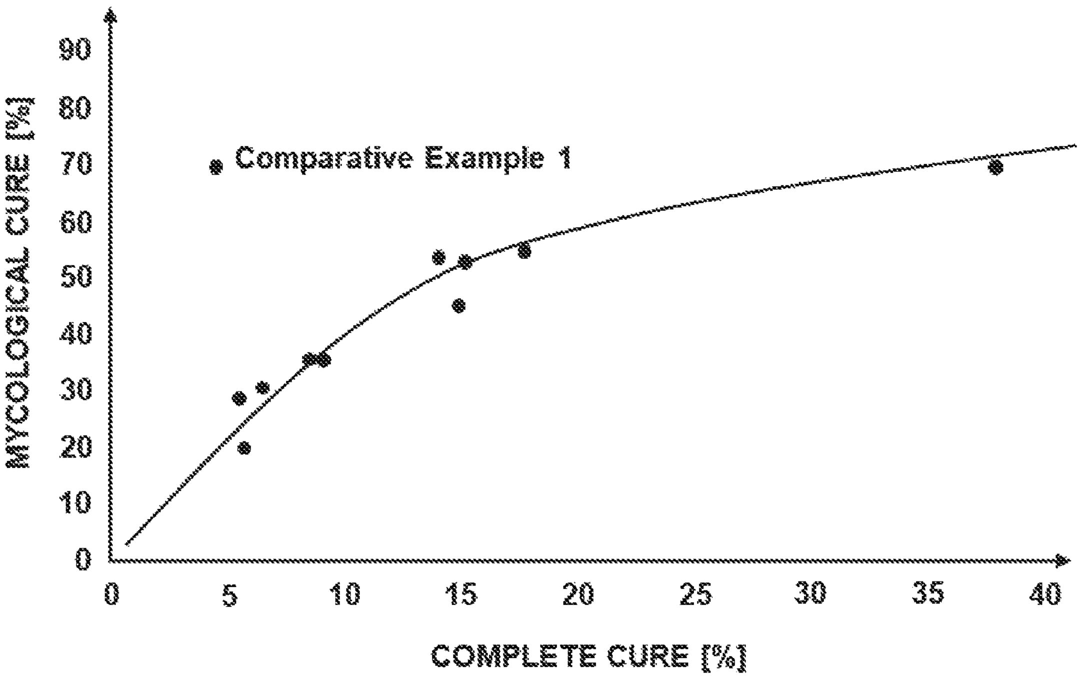
MYCOLOGICAL CURE [%]
90
80
70
60
50
40
30
20
10
0
Comparative Example 1
0
5
10
15
20
25
30
35
40
COMPLETE CURE [%]

TREATMENT REGIMEN FOR ONCHYOMYCOSIS USING ALLYLAMINE ANTIFUNGAL COMPOSITIONS

This application is a continuation of U.S. patent application Ser. No. 18/256,446, which is a national stage application under 35 U.S.C. § 371 of International Application No. PCT/GB2021/053195, filed Dec. 7, 2021, which claims the priority benefit of 63/122,588 filed Dec. 8, 2020.

FIELD OF THE INVENTION

This invention relates to new compositions and dosing regimens for the treatment of fungal infection of the nail by topical treatment, enabling efficient penetration of antifungal agents into and through the nail.

PRIOR ART AND BACKGROUND

The listing or discussion of an apparently prior-published document in this specification should not necessarily be taken as an acknowledgement that the document is part of the state of the art or common general knowledge.

Fungal infections of the nail (onychomycosis) and the associated damage of the nail affects about 2-5% of general population, increasing to 8-10% in persons over 50 years of age.

The topical treatment of onychomycosis has been the subject of considerable research effort. There are many potent antifungal drugs available, and there is a general understanding in the field that penetration of sufficient amounts of such compounds throughout the nail and into the nail bed will result in a cure.

However, nail infections remain very difficult diseases to treat precisely because the above objective is so difficult to achieve. As set out in 'Topical Absorption of Dermatological Products', Eds. Robert L Bronaugh and Howard Maibach, CRC Press, New York 2002 (Ying Sun, Jue-Chen Liu, Jonas C. T Wang and Piet De Doncker, Nail Penetration—Focus on Topical Delivery of Antifungal Drugs for Onychomycosis Treatment; Chapter 30 at pages 437-455, the lack of efficacy of topical treatment is likely due to the fact that antifungal drugs are unable to penetrate the nail plate to reach the infection sites, namely the nail plate, the nail bed and the nail matrix.

The thick nail plate, its dense keratinized nature, and the hyperkeratosis present in nail fungal infections make it a very difficult barrier for a topically applied drug to penetrate. Indeed, the structure of the nail allows only for hydration of the hard nail plate by water, allowing it to become more elastic and likely more permeable to a topically applied drug.

Because of this, most attempts to increase penetration of antifungal agents through the nail describe their topical administration in solutions containing water and other highly polar solvents. See, for example, U.S. Pat. No. 7,820,720, US patent applications US 2008/0188568 and US 2004/0096410, and international patent applications WO 2006/103638 and WO 2008/121709.

By contrast, international patent application WO 2012/107565 describes a novel formulation comprising the antifungal agent, terbinafine, in high amounts, in an essentially water-free vehicle comprising an organic acid, a diol and a sequestering agent, such as EDTA.

This document described how it was surprisingly found that the presence of the sequestering agent enables highly efficient penetration of the antifungal agent through the nail, a completely unexpected observation given that there is no known mechanism by which a sequestering agent such as EDTA would enhance nail penetrability of an active compound in a non-aqueous environment. Subsequent clinical trials demonstrated a mycological cure rate that was 54% after 48 weeks of treatment, which is remarkable for a topical treatment, for a composition of international patent application WO 2012/107565.

A more recently conducted North American Phase III clinical trial demonstrated that the same formulation achieved an even higher mycological cure rate, and that these high rates of mycological cure were surprisingly achieved in an early stage of the topical treatment, namely within the first few months.

However, the achieved levels of complete cure rates from the same Phase 3 trials were unexpectedly low. Complete cure includes both mycological cure and an assessment of the visual appearance of the nails (in terms of degree of restoration of the normal, or otherwise healthy, appearance of the nail). Data were outside of the expected relationship between mycological cure and complete cure that were previously seen for all commercial and development products.

Without being limited by theory, we believe that the tested formulation gave rise to excess hydration of the nail, which appeared as discoloration/whitening of the nails. In particular, this discoloration was generally observed as an increased whitening of the nail, which was distinct from discoloration associated with onychomycosis. This is what was subjectively perceived to give rise to slower restoration of the normal appearance of the nail.

In a second multinational Phase 3 clinical trial, the same formulation was compared to a topical formulation of 8% ciclopirox in the treatment of patients with mild to moderate distal subungual onychomycosis. The formulation achieved a very high rate of mycological cure (84% after 52 weeks compared to 42% for the ciclopirox formulation), but complete cure of the target nail was only 1.8% (compared to 1.6% for the ciclopirox formulation). Treatment was considered to be successful (treatment success; mycological cure and an acceptable appearance of the nail, i.e., ≤10% affected nail]) for 21.9% of patients receiving the formulation compared to 18.9% of the ciclopirox cohort. The unexpectedly low levels of complete cure and treatment success were again attributed to a whitening and discoloration of the nail, which was not observed in the ciclopirox cohort.

This ability of an essentially water-free composition to hydrate the nail to the degree necessary to cause discoloration/whitening was surprising given the very little water contained in the composition. However, even though the formulation was essentially water-free, it contained several ingredients which either in isolation or in combination promoted an unexpected hydration of the nail whilst in parallel promoting penetration of terbinafine through the nail.

It is understood by the inventors that this completely unexpected problem may be solved by:

(i) changing the application regimen for the formulation; and/or (ii) changing the formulation to promote an improved balance between nail penetration and nail hydration properties.

BRIEF DESCRIPTION OF THE DRAWING

FIG. 1 is a graph showing the cure rates achieved in this study presented in the accompanying Examples compared to the published results for other treatments shown in Table 2. The graph shows that the level of complete cure achieved in this study was surprisingly low and not consistent with the expected relationship between mycological cure and complete cure seen for other treatments.

DISCLOSURE OF THE INVENTION

Without being limited by theory, it is believed that a treatment regimen comprising a first 'loading' phase, during which the composition is applied frequently to the affected nail, followed by a 'maintenance' phase, during which the composition is applied less frequently, will cure the mycological infection and restore a healthy appearance of the nail, thereby achieving a high level of complete cure. It is believed that such a regimen will allow high levels of the active ingredient to build up in the nail tissue during the loading phase, which is a requirement for the effective treatment of the mycological infection.

The maintenance phase will maintain the active ingredient in the nail tissue while reducing the hydrating effects observed with more frequent treatment. This reduction in hydration is expected to reduce the discoloration and/or whitening of the nail caused by overhydration. Discoloration due to the effects of the formulation (e.g. overhydration) is generally observed as a whitening of the nail and therefore may be referred to herein as 'whitening discoloration'.

According to a first aspect of the invention there is provided a method of treatment of onychomycosis of the nail, which method comprises the steps of:

(a) a loading phase, which phase comprises the topical application to the nail of a pharmaceutically-acceptable composition comprising an antifungal allylamine compound at a frequency of least three times a week over a period of from about one to about six months; followed by (b) a maintenance phase, which phase comprises the topical application to the nail of a pharmaceutically-acceptable composition comprising an antifungal allylamine compound at a frequency of no more than two times per week as needed, wherein the pharmaceutically-acceptable composition comprising the antifungal allylamine compound comprises a non-aqueous solvent system.

The pharmaceutically-acceptable composition comprises a non-aqueous solvent system, that is capable of:

solubilizing the allylamine compound;

keeping said allylamine compound in solution both under normal storage conditions and when in use, and which solvent system is essentially water free.

Because the method of treatment according to the invention may take place over a long period of time, the antifungal allylamine needs to be present in the topical composition over such long period of time. If the active ingredient loses its integrity, either chemically or its physical form (e.g. by coming out of solution by way of precipitation) in will become inactive and the composition will lose its potency.

In this respect, the solvent system of the composition needs to be capable of not only dissolving the allylamine compounds but also keeping it in solution under normal storage conditions. This poses a challenge since the allylamine compounds are lipophilic and difficult to maintain in a stable solution.

It is known that allylamine antifungal compounds (such as terbinafine) have a tendency to precipitate over time in the presence of water if employed in amounts that are greater than about 1% w/w, such as about 3% w/w and especially greater than about 5% w/w, depending on the solvent system. If precipitation happens, an increasingly limited amount of active ingredient is present in solution to perform its therapeutic antifungal effect once applied to the nail.

In this respect, if an appropriate solvent system is selected that is both capable of dissolving an allylamine antifungal compound and is essentially free of water, a higher amount of allylamine antifungal agent may be employed, such as amounts that are at least about 5% w/w, such as at least about 7%, including at least about 10%, and at least about 12% or at least about 15%. By dissolving such high concentrations of allylamine and keeping such high concentrations in solution under normal storage conditions, it is possible to provide highly efficacious compositions for use in methods of treatments according to the invention.

Particular amounts of the allylamine antifungal compound (such as terbinafine) include amounts from about 5% w/w to about 15% w/w, such as from about 5% to about 12%, for example from about 7% to about 12% (e.g. from about 5% to about 10%).

Suitable allylamine antifungal compounds for use in the compositions include naftifine and, particularly, terbinafine.

The allylamine antifungal compound may be used (i.e. added to the composition) in the form of a pharmaceutically acceptable salt. In particular, the salt may be an acid addition salt, such as a hydrochloride salt.

Appropriate solvents should be liquid at room temperature and allow ready dissolution, and maintenance in solution under normal storage conditions, of the allylamine active ingredient at one of more of the abovementioned amounts.

In this respect, solvent systems may comprise one or more of an organic acid, organic acid esters, alkyl alcohols (including diols and triols) and mixtures thereof.

Organic acids that may be employed enable the provision (at the site of application of compositions of the invention) of a pH of between about 2.0 (e.g. about 3.5) and about 6.5. For the purpose of this invention, the term includes substances that are safe for use in mammals, such as weak acids. Typical pKas of weak acids are in the range of between about −1.5 (e.g. about −1.74, such as about 1.00, e.g. 2.00 and about 16 (e.g. about 15.74) (e.g. see Vollhardt, *Organic Chemistry* (1987)). A preferred range is between about 1 and about 10.

The organic acid component may thus comprise a $C_{1-10}$ carboxylic acid, which may be provided pure/neat and/or in (e.g. aqueous) solution. Examples of $C_{1-10}$ carboxylic acid include saturated and/or unsaturated, straight and/or branched aliphatic mono-, di- and polycarboxylic acids having 1, 2, 3, 4, 5, 6, 7, 8, 9 or 10 carbon atoms, alkylaryl or aromatic dicarboxylic acids, oxy and hydroxyl carboxylic acids (e.g. alpha-hydroxy acids) having 1, 2, 3, 4, 5, 6, 7 or 8 carbon atoms.

Examples of suitable organic acid components include one or more of formic acid, acetic acid, propionic acid, butyric acid, valeric acid, caproic acid, capryic acid, capric acid, sorbic acid, oxalic acid, hydroxybutyric acid, hydroxypropionic acid (e.g. 2-hydroxypropionic acid, hereinafter lactic acid), glycolic acid, citric acid, malic acid, tartaric acid, malonic acid, fumaric acid, succinic acid, glutaric acid, apidic acid, pimelic acid, oxalacetic acid, phthalic acid, tartronic acid and pyruvic acid. Preferred organic acids include hydroxy acids, such as hydroxybutyric acid, hydroxypropionic acids (e.g. lactic acid), glycolic acid, citric acid, malic acid and tartaric acid. More preferred organic acids include lactic acid. Lactic acid may be provided in e.g. a 90% aqueous solution.

Suitable esters of organic acids include $C_{1-4}$ alkyl esters of one or more of the forgoing organic acids. Preferred esters include esters of lactic acid, such as methyl lactate, ethyl lactate, butyl lactate and propyl lactate. Further preferred esters include $C_{1-4}$ alkyl esters of citric acid, malic acid and, particularly, acetic acid.

Alcohols may include monoalkyl alcohols, such as ethanol, propanol, butanol etc., or a triol, such as glycerol, but preferably the composition comprises at least one diol. Non-limiting examples of the diols include ethylene glycol, propylene glycol (propane-1,2-diol), butanediol, pentanediol (for example 1,5-pentanediol), hexanediol, and mixtures thereof. If desired, the diol component may be a mixture of diols such as a mixture of propylene glycol and another diol, such as 1,5-pentanediol. A preferred diol is propylene glycol.

It is preferred that a mixture of an organic acid and a diol form the bulk of the solvent system that is employed in the method of treatment according to the invention. When this mixture is employed, suitable concentration ratios of the organic acid component and the diol component may be between about 1:20 (acid: diol) and about 1:1, preferably from about 1:15 to about 1:2 and more preferably from about 1:12 to about 1:4, such as about 1:8 to about 1:5 (e.g. about 1:6), by weight based on the total weight of the composition.

When the bulk of the solvent system comprises a combination of organic acid and a diol component, the total amounts of these ingredients in the composition is preferably in the range of about 40% to about 80%, such as about 50% to about 70%, for example about 55% to about 65%.

It is further preferred that the composition that is employed in the method of treatment according to the invention is a one-phase solution in the form of a liquid that can be applied to the nail by an appropriate application means, that is, the solvent system that is employed is not a multiple- (e.g. two-) phase system such as an emulsion, including a homogenized emulsion or a microemulsion. The antifungal allylamine compound is preferably dissolved in this one-phase solvent system to form a one-phase liquid solution.

Other excipients that may be dissolved in the solvent system in addition to the active ingredient include a urea-based component. Such a urea-based component may comprise urea itself, and/or may comprise urea peroxide, also known as urea hydrogen peroxide (UHP), percarbamide or carbamide peroxide, which is an adduct of hydrogen peroxide and urea, and is used mainly as a disinfecting or bleaching agent in cosmetics and pharmaceuticals. We have found that the addition of urea peroxide improves the visual appearance of the nail more rapidly when such compositions of the invention are employed. This in turn leads to improved compliance; an improvement in appearance provides an incentive for the patient to continue treatment.

Another particularly preferred ingredient that may be employed in compositions of the invention is a sequestering (or sequestration) agent. We have found that the addition of a sequestration agent increases the delivery of allylamine antifungal agents into the nail. Suitable sequestering agents include of aminoacetic acids, phosphonates (e.g. sodium phosphonate), phosphonic acids (e.g. phosphonic acid) and mixtures of these. Sequestration agents can be metal complexing agents that may form a complex with metals such as the alkali metals or alkaline earth metals. A preferred aminoacetic acid is ethylenediaminetetraacetic acid (EDTA). When included in the compositions, examples of suitable amounts of the sequestering agent include from about 0.01 to about 5% by weight, such as from about 0.01% to about 1%, preferably from about 0.03% to about 0.5%.

As used herein (e.g. in the context of sequestering/sequestration agents), the term aminoacetic acid (and, similarly, aminoacetic acid sequestering agent) may be understood to refer to a metal complexing agent containing one or more amine and acetic acid moieties, such compounds containing two or more carboxyl groups, which are preferred, may also be referred to as aminopolycarboxylic acids. Examples of such compounds suitable for use in the compositions described herein include nitrolotriacetic acid (NTA), diethylenetriaminepentaacetic acid (DTPA) and, preferably, ethylenediaminetetraacetic acid (EDTA).

Other sequestering agents include phosphonic acids or phosphonates, or derivates thereof with amine. Examples of such compounds suitable for use include phosphonic acid, Ethylenediamine tetra(methylenephosphonic acid) (EDTMP) Hexamethylenediamine tetra(methylenephosphonic acid) (HDTMP) and, Diethylenetriamine penta(methylenephosphonic) acid (DTPMP).

Sequestering agents may be used in the form of salts (i.e. pharmaceutically acceptable salts), such as alkali metal or alkali earth metal salts. Particular salts that may be mentioned include sodium, potassium and calcium salts.

As hereinbefore described compositions that comprise the antifungal allylamine compound for use in methods of treatment according to the invention are non-aqueous, that is essentially water-free, which allows for the incorporation of high concentrations of allylamine compound in a one-phase solvent system, which high concentrations of dissolved active ingredient are retained during storage under normal storage conditions and in use.

Nevertheless, as stated above for lactic acid, some of the ingredients that may be employed in compositions that may be used in methods of treatment according to the invention may contain small amounts (including trace amounts) of water. Such small amounts of water may be present in the composition provided that they do not affect the stability of the composition (e.g. to precipitation of the active ingredient under normal storage conditions), as may be determined by the skilled person.

Furthermore, it is possible that the pH of the final composition may need to be raised to comply with e.g. regulatory requirements by the addition of a small amount of aqueous base (such as aqueous sodium hydroxide, e.g. 10M NaOH (aq.)). Final pHs of formulations are preferably in the range of about 3 to about 6 (e.g. about 4 to about 5.5, e.g. about 5.3 or less).

Apart from the foregoing, no additional water is added to the composition. The composition can tolerate up to about 6% water, such as up to about 5%, including up to about 4%, and more preferably comprises less than 3% of the composition based upon its total weight. As used herein, the phrase essentially water-free may also be understood to indicate that the composition contains sufficiently low amounts of water to prevent precipitation of the allylamine active ingredient (e.g. terbinafine).

In accordance with the invention, the pharmaceutically-acceptable composition comprising antifungal allylamine compound is applied as hereinbefore described during the loading phase over a period of about one month (e.g. about 4 weeks) to about six months (e.g. about 26 weeks), such as up to about 5 months, about 4 months or more preferably about 3 months (e.g. up to about 12 weeks). In particular, the loading phase may be for a period of about 8 weeks, about 10 weeks, about 12 weeks or about 24 weeks. More particularly, the loading phase may be for a period of 8 weeks, 10 weeks or 12 weeks (e.g. 8 weeks).

As herein, onychomycosis includes distal used subungual onychomycosis, white superficial onychomycosis, proximal subungual onychomycosis, endonyx onychomycosis and candidal onychomycosis. In particular, the onychomycosis to be treated is distal subungual onychomycosis (DSO). As used herein, distal subungual onychomycosis (DSO) may also be understood to include distal lateral subungual onychomycosis (DLSO).

This initial loading phase provides for 'intensive treatment' of onychomycosis with allylamine antifungal compounds to allow for the penetration and build-up of terbinafine within the nail region, that is the nail and the nail bed. Thus, application of the composition to the nail takes place at least three times per week, preferably at least four times per week, more preferably at least five times per week, such as at least six times per week, most preferably once or more times (e.g. twice) daily. In particular, the composition may be applied once daily.

Appropriate amounts of the composition, and therefore dosages of the active antifungal ingredient (e.g. terbinafine) to be applied to the nail/subject, will depend on the size and number of the affected nail(s), and may be determined by the person skilled in the art. The amount of the composition that each patient will use will thus greatly vary depending on these factors. However, from clinical trials, a typical daily amount for a single application to all toenails may be expected to be from about 0.2 ml to about 0.4 mL of the composition, while a patient with only one or a few toenails affected would use a significantly lower amount.

In particular, application of the composition may involve covering each affected nail, and under the nail edge, with a thin layer of the composition and allowing the nails to dry for approximately five minutes. The composition may also be applied to the skin surrounding the nail, including the lateral nail fold and proximal nail fold. Preferably, a period of at least 8 hours following application should be allowed to pass before washing the foot or hand undergoing treatment.

After the loading phase is complete, which may be prescribed by the label according to the method of treatment according to the invention, and/or varied by a physician or the otherwise skilled person in accordance with the severity, etc., application of the composition (which may be exactly the same composition or may be a different composition under the general definitions described herein), takes place with a maintenance phase regimen, in which the relevant composition is applied topically to the nail at a frequency of no more than twice per week, for as long as is needed.

This maintenance treatment has the dual purpose of maintaining high terbinafine levels within the nail unit, whilst at the same time allowing the nail to 'dry out' following its hydration during the loading phase.

The maintenance treatment may last between about two months (e.g. about 8 weeks) and about twelve months (e.g. about 48 weeks), such as up to about 9 months, including up to about 6 months, such as up to about 3 months or as required. In particular, the maintenance phase may last for about 12 weeks, about 24 weeks, about 26 weeks about 38 weeks or about 40 weeks. More particularly, the maintenance phase may last about 36 weeks, about 38 weeks or about 40 weeks (e.g. 40 weeks).

Maintenance treatment may also continue indefinitely if, for example, it is believed and/or expected that it will prevent relapse of the infection, which is a common issue in the treatment of onychomycosis.

During the maintenance phase, application of the composition will be less frequent such as once a week, once a fortnight down to once a month. In particular, the composition may be applied once a week.

Total treatment time in accordance with the invention may typically vary between about 16 weeks and about 52 weeks. However, maintenance treatment may continue after this period as appropriate.

In particular, the total treatment time may be for 48 weeks, which is the standard treatment term for topical treatment of fungal nail infections. Again, maintenance treatment may continue after this period as appropriate.

Particular treatment regimens that may be mentioned include those in which the loading phase is for a period of 8, 10 or 12 weeks during which the composition is applied once daily and the maintenance phase is for a period of 36, 38 or 40 weeks during which the composition is applied once weekly. Preferably, total treatment time is for a period of 48 weeks corresponding to a loading phase of 8 weeks followed by a maintenance phase of 40 weeks or a loading phase of 10 weeks followed by a maintenance phase of 38 weeks or a loading phase of 12 weeks followed by a maintenance phase of 36 weeks.

Further treatment regimens that may be mentioned include those in which the loading phase is for a period of 12 or 24 weeks during which the composition is applied once daily and the maintenance phase is for a period of 12, 24 or 36 weeks during which the composition is applied once weekly. Preferably, total treatment time is for a period of 48 weeks corresponding to a loading phase of 12 weeks followed by a maintenance phase of 36 weeks or a loading phase of 24 weeks followed by a maintenance phase of 24 weeks.

Compositions that may be used in the methods described herein include those described herein.

Particular compositions that may be mentioned include compositions comprising:

(i) an antifungal allylamine compound (e.g. terbinafine) in an amount of at least about 5% w/w;
(ii) a diol component (e.g. propane-1,2-diol) in an amount of more than 50% w/w;
(iii) an organic acid component (e.g. lactic acid) in an amount of about 5% w/w to about 25% w/w; and
(iv) a sequestering agent (e.g. EDTA) in an amount of from about 0.03% w/w to about 0.5% w/w.

More particular compositions include compositions comprising:

(i) an antifungal allylamine compound (e.g. terbinafine, or a pharmaceutically acceptable salt thereof) in an amount of from about 8% w/w to about 12% w/w;
(ii) a diol component (e.g. propane-1,2-diol) in an amount of from about 50% w/w to about 70% w/w;
(iii) a organic acid component (e.g. lactic acid) in an amount of from about 5% w/w to about 15% w/w;
(iv) a sequestering agent (e.g EDTA, or a pharmaceutically acceptable salt thereof) in an amount of from about 0.03% w/w to about 0.1% w/w; and
(v) a urea-based component (e.g. urea) in an amount of between about 15% w/w to about 25% w/w, such compositions may further comprise aqueous base (such as aqueous sodium hydroxide, e.g. 10M NaOH (aq.)).

A particular composition for use in the methods of the invention comprises (or consists essentially of):

(i) terbinafine hydrochloride in an amount of about 10% (w/w);
(ii) propane-1,2-diol in an amount of about 60% (w/w);

(iii) lactic acid in an amount of about 9% (w/w);

(iv) EDTA;

(v) urea;

(vi) 10 M aqueous sodium hydroxide solution.

A further particular composition for use in the methods of the invention comprises (or, preferably, consists essentially of or consists of):

(i) terbinafine hydrochloride in an amount of 10% (w/w);

(ii) propane-1,2-diol in an amount of 59.7% (w/w);

(iii) lactic acid in an amount of 9% (w/w);

(iv) EDTA in an amount of 0.05% (w/w);

(v) urea in an amount of 18% (w/w); and (vi) 10M aqueous sodium hydroxide solution.

For the avoidance of doubt, % (w/w) takes its normal meaning in the art and indicates the amount of a component by weight as a percentage of the total weight of the composition.

Further compositions that may be mentioned include the compositions of the invention described hereinafter.

We submit that decreasing the total dose of composition, i.e. decreasing the intensity of the treatment, in order to improve appearance of the nail and thus the complete cure while at the same time maintaining a high rate of mycological cure is counterintuitive. Typical recommended dosage of currently-prescribed topical treatments against onychomycosis includes daily application for a year or more in order to achieve full mycological cure. In other words, intensive treatment over a prolonged period is considered necessary to achieve as full mycological cure as possible and to allow restoration of the nail appearance.

However, in view of the high levels of early mycological cure reported in the aforementioned clinical studies for the above compositions as well as data obtained close to the end of the study, which show that nail appearance improves after once treatment is stopped, as described hereinafter, we believe that this such prolonged intensive treatment is not necessary for the compositions to achieve mycological cure. Thus, the compositions are expected to achieve complete cure when applied to the nail in accordance with the method of treatment according to the invention.

The invention also relates to novel antifungal compositions (formulations) that give rise to an improved restoration of the normal (or healthy) appearance of the nail compared to the compositions mentioned above, and therefore achieve a higher level of complete cure as a result of the treatment. Without being limited by theory, it is believed that the novel compositions may reduce the degree of hydration of the affected nails during the course of the treatment, which may lead to a reduction in the degree of discoloration and/or whitening (e.g. whitening discoloration) of the nail being observed during and/or after completion of the treatment.

The novel compositions comprise a non-aqueous (essentially water free) solvent system in which an antifungal allylamine compound, such as terbinafine, is dissolved, and are, preferably, in the form of a one-phase liquid solution, as described hereinbefore.

These novel compositions, including all aspects, embodiments, particular and preferred features described hereinafter may be referred to as 'the compositions of the invention'.

According to a further aspect of the invention, there is provided a pharmaceutical composition comprising:

(i) an allylamine antifungal compound in an amount of at least about 5% w/w;

(ii) an organic acid component in an amount of about 1% w/w to about 20% w/w;

(iii) a diol component in an amount of about 10% w/w to about 50% w/w;

(iv) a monoalcohol component in an amount of about 10% w/w to about 40% w/w; wherein the composition is essentially water-free.

For the avoidance of doubt, suitable allylamine antifungal compounds, organic acids and diols, and amounts thereof, that may be employed as components of the compositions include those defined hereinbefore (i.e. in respect of the first aspect of the invention, including all embodiments and particular features thereof), including mixtures thereof.

The compositions of the invention (including all aspects thereof) are essentially water free, which allows for the incorporation of a high concentration of the allylamine antifungal compound in a one-phase solvent system as described hereinbefore. However, again as described hereinbefore, the compositions can tolerate, and therefore may contain, small amounts of water. Aqueous base (such as NaOH) may also be added to the compositions for the purpose of pH adjustment.

Such small amounts of water include up to about 6%, such as up to about 5%, including up to about 4%, and more preferably comprises less than 3% of the composition based upon its total weight. These amounts may be included provided that the composition contains sufficiently low amounts of water to prevent precipitation of the allylamine active ingredient (e.g. terbinafine).

The compositions of the invention (including all aspects thereof) are suitable for application to the nails and the surrounding skin, including, particularly, the lateral nail fold and proximal nail fold, as is conventional for a topically-applied nail treatment.

In particular, the antifungal allylamine compound is terbinafine (or a pharmaceutically acceptable salt thereof (e.g. a HCl salt)), which may be present in an amount of from about 5% w/w to about 15% w/w, such as from about 5% and to about 12%, for example from about 8% to about 12% or from about 5% to about 10%).

The organic acid component is one or more $C_{1-10}$ carboxylic acid, which may be provided pure/neat and/or in (e.g. aqueous) solution. Thus, the carboxylic acid component may alternatively be referred to as a $C_{1-10}$ organic acid component. Examples of $C_{1-10}$ carboxylic acid include saturated and/or unsaturated, straight and/or branched aliphatic mono-, di- and polycarboxylic acids having 1, 2, 3, 4, 5, 6, 7, 8, 9 or 10 carbon atoms, alkylaryl or aromatic dicarboxylic acids, oxy and hydroxyl carboxylic acids (e.g. alpha-hydroxy acids) having 1, 2, 3, 4, 5, 6, 7 or 8 carbon atoms.

The organic acid component preferably comprises lactic acid. More particularly, the organic acid component is selected from the group consisting of lactic acid, citric acid, pentanoic acid and mixtures thereof. In certain embodiments, the organic acid component is lactic acid. In particular, the organic acid component may be present in the compositions in an amount of from about 3% w/w to about 15% w/w, preferably about 5% to about 15%, such as from about 3% to about 10%, for example from about 3% to about 8% (e.g. about 5% w/w).

For the avoidance of doubt, where it is stated that a component of the composition is a particular compound (or selected from a group of particular compounds), it may be understood that the relevant component of the composition consists essentially of that compound (or compounds). However, it is envisaged that the components of the compositions may added to the compositions in any suitable form to produce a stable composition. For example, organic acids may be provided in aqueous solutions and the antifungal allylamine compound may be provided in the form of a pharmaceutically acceptable salt. In such instances, 'consists essentially of' may be understood to refer to the compound or compounds in the form that it is supplied (e.g. as a solution/salt, as appropriate).

The diol component may particularly be selected from the group consisting of propanediol, butanediol, pentanediol and mixtures thereof. Preferably, the diol component is selected from propane-1,2-diol (propylene glycol), propane-1,3-diol and mixtures thereof. In certain embodiments, the diol component is propane-1,2-diol (propylene glycol). In particular, the diol component may be present in an amount of from about 10% w/w to about 45% w/w, more particularly, from about 15% to about 35%, such as from about 20% to about 35%, for example from about 20% to about 30%.

The monoalcohol component may comprise alcohols selected from ethanol, propanol (including 1-propanol and 2-propanol (iso-propanol)) and butanol (including 1-butanol, 2-butanol iso-butanol and tert-butanol). Preferably, the monoalcohol component comprises ethanol. More particularly, the monoalcohol component is selected from ethanol, iso-propanol and mixtures thereof. In certain embodiments, the monoalcohol component is ethanol. In particular, the monoalcohol component may be present in an amount of from about 15% w/w to about 35% w/w, such as from about 20% w/w to about 30% w/w.

In particular embodiments, the compositions may further comprise a sequestering agent in an amount of about 0.01% w/w to about 1% w/w.

Suitable sequestering agents that may be employed in the compositions include those defined hereinbefore (i.e. in respect of the first aspect of the invention, including all embodiments and particular features thereof), including mixtures thereof. The sequestering agent is preferably selected from an aminoacetic acid (e.g. EDTA, or a pharmaceutically acceptable salt thereof (e.g. sodium or calcium salts)) and a phosphonate (e.g. sodium phosphonate.). In particular, the sequestering agent may be an aminoacetic acid. More preferably, the sequestering agent is EDTA, or a pharmaceutically acceptable salt thereof. The sequestering agent may, preferably, be present in an amount of from about 0.03% w/w to about 0.5% w/w, such as from about 0.05% w/w to about 0.2% w/w.

In particular embodiments, the compositions may further comprise a urea-based component, which component is preferably included in an amount of about 5% w/w to about 25% w/w, such as from about 5% to about 20%, for example about 10% to about 20%, or from about 5% to about 15%, for example from about 5% to about 10% (e.g. about 10%). The urea-based component may comprise urea itself and/or urea peroxide. Preferably, the urea-based component is urea itself.

The compositions may also further comprise an organic acid ester component, which component is preferably included in an amount of about 5% w/w to about 30% w/w. Suitable esters include those defined hereinbefore (i.e. in respect of the first aspect of the invention, including all embodiments and particular features thereof). Preferred esters include ethyl and iso-propyl esters. Preferred organic ester components include those listed hereinbefore (i.e. esters of lactic acid), and, particularly, ethyl lactate and iso-propyl lactate. In particular, the organic acid ester component may be included in an amount of from about 5% w/w to about 25% w/w, such as from about 5% to about 20%, for example from about 10% to about 20%.

The compositions may also further comprise a $C_{12-22}$ fatty acid component in an amount of from about 1% w/w to about 10% w/w (such as from about 2% to about 5%). Suitable $C_{12-22}$ fatty acids include saturated and unsaturated fatty acids. Particular $C_{12-22}$ fatty acid components that may be mentioned include one or more of lauric acid, myristic acid, oleic acid, linoleic acid and linolenic acid. When a $C_{12-22}$ fatty acid component is present, it is preferred that the total amount of the $C_{12-22}$ fatty acid component and the organic acid component is from about 1% w/w and about 20% w/w (such as from about 5% w/w to about 20% w/w).

Without being bound by theory, it is believed that certain components may contribute to the undesirable discoloration/whitening of the nails observed following treatment with the earlier composition due to their hygroscopicity, low volatility and/or other relevant physical properties. In particular, it is believed that the diol component, organic acid component and, if present, the urea-based component may contribute to this effect. Accordingly, it is desirable to limit the amounts of these components present in the compositions.

Thus, the organic acid component and diol component collectively may be present in an amount of about 55% w/w or less, such as about 50% or less, for example about 45% or less, e.g. about 40% w/w or less. In particular, the organic acid component and diol component may collectively be present in an amount of from about 20% w/w to about 50% w/w, such as from about 20% w/w to about 45% w/w, for example from about 20% w/w to about 40% w/w.

For compositions comprising a urea-based component, the organic acid component, diol component and urea-based component collectively may be present in an amount of 65% w/w or less, such as about 60% or less, for example about 55% or less, e.g. about 50% or less. In particular, the organic acid component, diol component and urea-based component collectively may be present in an amount of about 25% w/w to about 60% w/w, such as from about 25% w/w to about 55% w/w, for example from about 25% w/w to about 50% w/w, e.g. from about 25% w/w to about 45% w/w.

The remaining mass of the compositions may be made up by other appropriate excipients as known to the person skilled in the art. In particular, the monoalcohol component and the organic ester components described herein.

For composition comprising a urea-based component (e.g. urea), it is preferred that the urea-based component and organic acid component are present in a ratio of about between about 5:1 and about 1:1 (urea-based component: organic acid component), such as between about 4:1 and about 1:1, for example about 2:1 to about 1:1.

In a further aspect of the invention, there is provided a pharmaceutical composition comprising:

(i) an allylamine antifungal compound in an amount of at least about 5% w/w;

(ii) an organic acid component in an amount of about 1% w/w to about 20% w/w;

(iii) a diol component in an amount of about 10% w/w to about 50% w/w;

wherein the composition is essentially water free, and wherein the organic acid component and diol component are collectively present in an amount of about 20% w/w to about 50% w/w, such as from about 20% w/w to about 45% w/w, for example from about 20% w/w to about 40% w/w.

Such compositions may further comprise a urea-based component which component is preferably included in an amount of about 5% w/w to about 25% w/w. In such compositions, it is preferred that the organic acid component, diol component and urea-based component collectively are present in an amount of 65% w/w or less, such as about 60% or less, for example about 55% or less, e.g. about 50% or less. In particular, the organic acid, diol component and urea-based component collectively may be present in an amount of about 25% w/w to about 60% w/w, such as from about 30% w/w to about 55% w/w, for example from about 30% w/w to about 50% w/w.

Such compositions may further comprise a sequestering agent in an amount of about 0.01% w/w to about 1% w/w.

In a further aspect of the invention, there is provided a pharmaceutical composition comprising:

(i) an allylamine antifungal compound in an amount of at least about 5% w/w;

(ii) an organic acid component in an amount of about 1% w/w to about 20% w/w;

(iii) a diol component in an amount of about 10% w/w to about 50% w/w;

and one or more component selected from:

(iv) a monoalcohol component in an amount of about 10% w/w to about 40% w/w; and (v) an organic acid ester component in an amount of about 5% w/w to about 30% w/w;

wherein the composition is essentially water free, and wherein the organic acid component and diol component are collectively present in an amount of about 20% w/w to about 50% w/w, such as from about 20% w/w to about 45% w/w, for example from about 20% w/w to about 40% w/w.

Such compositions may further comprise a urea-based component which component is preferably included in an amount of about 5% w/w to about 25% w/w. In such compositions, it is preferred that the organic acid component, diol component and urea-based component collectively are present in an amount of 65% w/w or less, such as about 60% or less, for example about 55% or less, e.g. about 50% or less. In particular, the organic acid, diol component and urea-based component collectively may be present in an amount of about 25% w/w to about 60% w/w, such as from about 30% w/w to about 55% w/w, for example from about 30% w/w to about 50% w/w.

Such compositions may further comprise a sequestering agent in an amount of about 0.01% w/w to about 1% w/w.

Such compositions may also further comprise a $C_{12-22}$ fatty acid component in an amount of from about 1% w/w to about 10% w/w.

It is preferred that such compositions comprise a monoalcohol component or both a monoalcohol component and an organic acid ester component. In particular embodiments, both of these components are present in the compositions.

For the avoidance of doubt, unless context suggests otherwise, it is envisaged that the compositions of the different aspects of the compositions of the invention may be combined with any of the particular and preferred features of the invention as described herein (such as the amounts and identities of the components of the compositions) in particular those features described with reference to the compositions of the invention.

Further compositions in accordance with the invention comprise a surfactant component in combination with an allylamine antifungal compound, a sequestering agent, an organic acid component, a diol component, and organic ester component and, optionally, a urea-based component. Again, without wishing to be limited by theory, it is believed that including a surfactant component, particularly in combination with more lipophilic components, may reduce uptake of water into the nail in the course of treatment and thereby lead to a reduced degree of discoloration/whitening during and/or after completion of the treatment.

Thus, in a further aspect of the invention, there is provided a pharmaceutical composition comprising:

(i) an allylamine antifungal compound in an amount of at least about 5% w/w;

(ii) an organic acid component in an amount of from about 1% to about 20% w/w;

(iii) a diol component in an amount of from about 10% w/w to about 60% w/w (iv) an organic ester component in an amount of about 5% w/w to about 45% w/w; and (v) a surfactant component in an amount of from about 1% w/w to about 15% w/w;

wherein the composition is essentially water free.

For the avoidance of doubt, suitable allylamine antifungal compounds, sequestering agents, organic acids and diols that may be employed as components of the compositions include those defined hereinbefore (e.g. in respect of the first aspect of the invention, including all embodiments and particular features thereof), including mixtures thereof.

In particular, in the compositions of this aspect of the compositions of the invention, the antifungal allylamine compound is terbinafine (or a pharmaceutically acceptable salt thereof (e.g. a HCl salt)), which may be present in an amount of from about 5% w/w to about 15% w/w, such as from about 5% and to about 12%, for example from about 8% to about 12%, or from about 5% to about 10%.

The organic acid component preferably comprises lactic acid. More particularly, the organic acid component is selected from the group consisting of lactic acid, citric acid, pentanoic acid and mixtures thereof. In certain embodiments, the organic acid component is lactic acid. In particular, the organic acid component may be present in the compositions in an amount of from about 3% w/w to about 15% w/w, preferably about 5% to about 15%, such as from about 3% to about 10%, for example from about 3% to about 8% (e.g. about 5% w/w).

Diols suitable for use in this aspect of the compositions of the invention include ethane-1,2-diol (ethylene glycol), propanediol, butanediol, pentanediol and mixtures thereof. Preferably, the diol component is selected from the group consisting of ethane-1,2-diol, propane-1,2-diol and mixtures thereof. In particular, the diol component may be present in an amount of from about 20% w/w to about 55% w/w, such as from about 20% to about 50%, for example from about 20% to about 40%.

Suitable esters for the organic ester component include those described hereinbefore. More particularly, the organic ester component may be an alkyl ester of acetic acid or a mixture of such esters. Preferably, the organic ester component is selected from ethyl acetate, propyl acetate (e.g. n-propyl acetate), butyl acetate (e.g. n-butyl acetate) and mixtures thereof. In particular, the organic acid ester component is included in an amount of from about 5% w/w to about 35% w/w, such as from about 10% w/w to about 35% w/w.

In particular embodiments, the organic ester component may further comprise one or more ester of a $C_{12-22}$ fatty acid in an amount of from about 1% to about 10% (such as about 2% to about 5%). Suitable esters include $C_{1-4}$ alkyl esters. Particular esters that may be mentioned include methyl, ethyl and propyl esters of lauric acid, myristic acid, oleic acid, linoleic acid and linolenic acid.

Suitable surfactants for use in the compositions of this aspect of the invention include ethoxylated sorbitan esters (polysorbates) (such as polysorbate 60 and polysorbate 80), sorbitan fatty acid esters (such as sorbitan monooleate and sorbitan monolaurate), ethoxylated alkyl ethers or esters (such as castor oil ethoxylates, lauric acid ethoxylate, lauryl alcohol ethoxylate, oleic acid ethoxylate), polyoxylated glycerides, nonionic triblock copolymers (poloxamers) (such as polyethylene oxide-polypropylene oxide-polyethylene oxide (PEO—PPO-PEO) triblock copolymers and polypropylene oxide-polyethylene oxide-polypropylene oxide (PPO-PEO-PPO) triblock copolymers), monoglycerides (such as glycerol monolaurates, glycerol monostearate and glycerol hydroxymonostearate), lecithin (such as egg lecithin and soy lecithin) and mixtures thereof. Preferably, the surfactant component is selected from polysorbate 60, polysorbate 80, lecithin, monoglycerides and mixtures thereof. In particular, the surfactant component is present in an amount of from about 3% w/w to about 12% w/w, such from about 5% w/w to about 10% w/w.

In particular embodiments, the compositions may further comprise a sequestering agent in an amount of about 0.01% w/w to about 1% w/w.

The sequestering agent in the compositions of this aspect of the invention is preferably selected from an aminoacetic acid (e.g EDTA, or a pharmaceutically acceptable salt thereof (e.g. sodium or calcium salts)) and a phosphonate (e.g. sodium phosphonate.). In particular, the sequestering agent may be an aminoacetic acid. More preferably, the sequestering agent is EDTA, or a pharmaceutically acceptable salt thereof (e.g. sodium or calcium salts). The sequestering agent may, preferably, be present in an amount of from about 0.03% w/w to about 0.5% w/w, such as from about 0.05% w/w to about 0.2% w/w.

In particular embodiments, the compositions of this aspect may further comprise a urea-based component, which component is preferably included in an amount of about 5% w/w to about 25% w/w, such as from about 5% to about 20%, for example about 10% to about 20%, or from about 5% to about 15%, for example from about 5% to about 10% (e.g. about 10%). The urea-based component may comprise urea itself and/or urea peroxide. Preferably, the urea-based component is urea itself.

The of compositions of this aspect may also comprise a lipid component in an amount of 0.5% to about 5%. The lipid component may be a polar lipid such as a diglyceride or a mixture of mono and diglycerides (such as mixtures of glycerol monolaurate and glyceryl dilaurate or glycerol, or glycerol monoleate and glyceryl dioleate) or an apolar lipid such as a triglyceride (such as triglycerides derived from soybean oil, MCT (Medium Chain Triglycerides)-oil or castor oil).

As for other compositions of the invention, it is believed that it is desirable to limit the amounts of the organic acid, diol, and, if present, urea-based components of the compositions of this aspect as these components are thought to contribute to the whitening/discoloration of the nail. Thus, the limitations on the combined amounts of these components described hereinbefore apply equally to the compositions of this aspect of the invention. In particular, the organic acid component and diol component may collectively be present in an amount of from about 20% w/w to about 50% w/w, such as from about 20% w/w to about 45% w/w, for example from about 20% w/w to about 40% w/w and, if a urea-based component is included in the composition, the organic acid component, diol component and urea-based component collectively may be present in an amount of about 25% w/w to about 60% w/w, such as from about 25% w/w to about 55% w/w, for example from about 35% w/w to about 50% w/w, e.g. from about 25% w/w to about 45% w/w.

The compositions of the invention (including all aspects thereof) may further include a triol component, such as glycerol, in an amount of from about 1% w/w to about 15% w/w, such from about 3% to about 10%, for example from about 5% to about 10%, e.g. about 5% w/w.

In compositions comprising a triol component, the organic acid component, diol component, triol component and, if present the urea-based component, may collectively be present in an amount of 65% w/w or less, such as from about 60% w/w or less, for example about 55% w/w or less, e.g. about 50% w/w or less. In particular, the organic acid, diol component and triol component collectively may be present in an amount of about 25% w/w to about 60% w/w, such as from about 30% w/w to about 55% w/w, for example from about 30% w/w to about 50% w/w.

As described hereinbefore, it is possible that the pH of the final compositions may need to be raised to comply with e.g. regulatory requirements by the addition of a small amount of aqueous base (such as aqueous sodium hydroxide, e.g. 10M NaOH (aq.)). The stability of the solution may also be influenced by the pH. Final pHs of formulations are preferably in the range of about 3 to about 6 (e.g. about 4 to about 5.5, e.g. about 5.3 or less). Accordingly, the compositions may contain about 1% to about 3% (e.g. 1%) aqueous base (e.g. 5M NaOH or 10M NaOH). Alternatively, a base (e.g. NaOH) may be added to the compositions in solid form.

Compositions of the invention may further comprise additional pharmaceutically acceptable carriers and excipients, such as stabilisers, other penetration enhancers and coloring agents.

Compositions of the invention may be prepared by standard techniques, and using standard equipment, known to the skilled person. Other ingredients may be incorporated by standard mixing or other formulation principles.

Compositions of the invention may thus be incorporated into various kinds of pharmaceutical preparations intended for topical administration using standard techniques (see, for example, Lachman et al., "*The Theory and Practice of Industrial Pharmacy*", Lea & Febiger, 3rd edition (1986) and "*Remington: The Science and Practice of Pharmacy*", Gennaro (ed.), Philadelphia College of Pharmacy & Sciences, 19th edition (1995)), by combining compositions of the invention with conventional pharmaceutical additives and/or excipients used in the art for such preparations.

Compositions of the invention are preferably administered directly to the nail and/or skin. For instance, the composition is administered on and around a human toenail or fingernail affected by a fungal disease, such as onychomycosis. This may be performed by covering each affected nail with a liquid/solution composition from about twice or three times per day to about once per week with a layer of the composition.

The composition may also be applied to the edge of a nail or to the lateral aspects of the nail (lateral nail fold) or to the proximal nail fold. Administration of such a composition may be achieved by means of a suitable device such as a drop tip, a small brush or a spatula.

Compositions of the invention demonstrate high penetration into e.g. the nail. This can be assessed by an in vitro method for nail penetration. For example, a Franz cell can be used to study the penetration through a membrane from a bovine hoof or other suitable model membranes such as human cadaver nails.

In a further aspect of the invention there is provide a method of treatment of onychomycosis of a nail, which method comprises administering (e.g. topically) a therapeutically effective amount of a composition of the invention to a patient in need thereof.

In a further aspect of the invention there is provided a method of treatment of onychomycosis of the nail as hereinbefore defined in relation to the first aspect of the invention, wherein the pharmaceutical composition used in the method is a composition of the invention as defined herein.

By "treatment" we include the therapeutic and/or cosmetic treatment, as well as the curative symptomatic, prophylactic or maintenance and palliative treatment of the disease. Treatment thus includes the alleviation of symptoms of fungal diseases, treatment of the fungal infection and the improvement in the appearance of nails and/or skin. In particular, the methods of treatment described herein may achieve a mycological cure (i.e. eradication of the fungal infection), while also restoring the normal or near normal (or an otherwise healthy/clinically acceptable) appearance of the nail and thereby achieving a complete cure of the infection.

When used herein in relation to a specific value (such as an amount, a period of time or a percentage), the term 'about' (or similar terms, such as 'approximately') may be understood as indicating that such values may vary by up to 10% (particularly, up to 5%, such as up to 1%) of the value defined. It is contemplated that, at each instance, such terms may be replaced with the notation '±10%', or the like (or by indicating a variance of a specific amount calculated based on the relevant value). It is also contemplated that, at each instance, such terms may be deleted.

Mycological cure may be assessed by producing a fungal culture of dermatophytes from the affected nail and/or by direct KOH microscopy or a KOH microscopy where fluorescent dyes are added to improve detection. A negative result in one or, preferably, both of these assessments is indicative of mycological cure being achieved. If a nail is assessed by both fungal culture and KOH microscopy, a negative result in both assessments is normally considered to be required to show that mycological cure has been achieved. Other methods for assessing mycological cure are also possible to use, such as applying techniques of PCR (Polymerase Chain Reaction) and/or PAS periodic acid-Schiff) stain. In order to achieve complete cure of the infection, in addition to achieving a mycological cure it is necessary for there to be no visible signs of infection (which may be referred to as a 'clinical cure' of the infection).

Determination of complete cure involves a visual inspection of the nail by an appropriately trained and experienced healthcare professional (e.g. a physician or podiatrist).

The methods and compositions described herein have the advantage that they achieve an increased complete cure rate in the treatment of onychomycosis compared to prior art compositions and methods.

The methods and compositions described herein may also have the advantage that they may be more efficacious than, be less toxic than, be longer acting than, be more potent than, have greater patient compliance than, delay recurrence, cause greater patient satisfaction than, produce fewer side effects than, possess a better patient acceptability than and have a better pharmaceutical profile than equivalent methods and compositions known in the prior art. The compositions may also be more easily absorbed than, and/or have other useful pharmacological, physical, or chemical properties over, pharmaceutical compositions known in the prior art, whether for use in the treatment of nail diseases or otherwise.

EXAMPLES

The invention will be further described by reference to the following examples, which are not intended to limit the scope of the invention.

Comparative Example 1

Clinical Study

A composition containing terbinafine hydrochloride (10% w/w), propane-1,2-diol (59.7% w/w), lactic acid (9% w/w), EDTA (0.05% w/w), urea (18% w/w) and aqueous 10M sodium hydroxide solution (and no other components) was assessed for efficacy and safety as a topical treatment of mild to moderate distal subungual onychomycosis (DSO) in a multi-centre, double-blind, randomized, vehicle-controlled clinical trial.

The subjects (n=365) were split into two unequal treatment groups. The first (n=285) received the above-described composition and the second (n=119) received the vehicle control (the composition without the active ingredient terbinafine). The treatments were applied to all affected fingernails and toenails, but fingernails were not assessed for efficacy. A target toenail (large toenail) for the assessment of efficacy was selected for each subject and followed throughout the study.

For inclusion in the study, subjects had to be between 12 and 75 years of age and have DSO of at least one of the great toenail(s) affecting 20% to 60% of the target nail (evaluated by a central blind assessor on the basis standardized photo documentation, and diagnosis of DSO confirmed through a positive culture of dermatophytes).

The treatments were applied topically to cover all affected toenails and fingernails with a thin layer and under the free edge of the nails, once daily for a period of 48 weeks. The compositions were applied during the evening and allowed to dry for approximately 5 minutes after application. The first application of the compositions was performed on site and under supervision. Any nails other than the target toenail that were considered by the investigator to be clinically cured before week 48, were not treated further after clinical cure, and therefore complete cure, was achieved.

Of the 365 randomized subjects, 305 (83.6%) were male and 60 (16.4% were female). The subjects were between 12 and 74 years of age, with an average (mean) age of 55.0, and the majority of subjects were white (85.4% (treatment group), 89.1% vehicle control and 86.6% overall). The target toenail was on the left foot for 50.7% (49.6% treatment group; 52.9% vehicle control group) of the subjects and the right foot for 49.4% (50.4% treatment group; 47.1% vehicle control group) of the subjects.

The rates of complete cure and mycological cure of the target toenails were assessed at week 52 (four weeks after completion of the treatment). There were 47 dropouts within the treatment group and 31 dropouts within the control group. In addition to this, a further 26 patients (18 treatment group; 8 control group) were judged to have had a <80% compliance rate with the treatment regime and 8 others (5 treatment group; 3 control group) were considered to have majorly deviated from the treatment protocol. However, all of these subjects were included in the full analysis set for the assessment of efficacy.

Mycological cure was defined as negative fungal culture of dermatophytes and negative direct KOH microscopy of the target toenail. Complete cure was defined as mycological cure and 0% clinical disease involvement of the target toenail. The rates of complete cure and mycological cure achieved are shown in Table 1.

TABLE 1

| | Treatment group (n = 246) | Control group (n = 119) | Total (n = 365) |
|---|---|---|---|
| | Complete Cure | | |
| n (%) | 11 (4.5%) | 0 (0.0%) | Diff. 4.5% |
| 95% CI | 2.3:7.9 | 0.0:3.1 | 1.9:7.1 |
| p-value Cochran Mantel Haenszel | | | 0.0195 |
| p-value Chi square | | | 0.0192 |
| | Mycological cure | | |
| n (%) | 172 (69.9%) | 33 (27.7%) | Diff: 42.2% |
| 96.25% CI | 63.4:75.9 | 19.5:37.2 | 31.7:52.7 |
| p-value Cochran Mantel Haenszel | | | <0.001 |
| p-value Chi square | | | <0.001 |

Overall, a high mycological cure rate was achieved, but the complete cure rate was unexpectedly low. The mycological cure rate was substantially higher than mycological cure rates achieved for other approved topical treatments and at the same level as oral terbinafine. The low complete cure rate is inconsistent with the mycological cure rate, as a high mycological cure rate is usually associated with a high complete cure rate.

For comparison, the reported mycological cure and complete cure rates from clinical studies into other treatments for DSO are shown in Table 2.

TABLE 2

| Treatment | Complete Cure (%) | Mycological Cure (%) |
|---|---|---|
| Ciclopirox (Penlac ®) Study 1[1] | 5.5 | 29 |
| Ciclopirox (Penlac ®) Study 2[1] | 8.5 | 36 |
| Efinaconazole (JUBLIA ®) Study 1[2] | 15.2 | 53.4 |
| Efinaconazole (JUBLIA ®) Study 2[2] | 17.8 | 55.2 |
| Tavaborole (KERYDIN ®) Study 1[3] | 6.5 | 31 |
| Tavaborole (KERYDIN ®) Study 2[3] | 9.1 | 35.9 |
| Terbinafine (oral) (LAMISIL ®)[4] | 38 | 70 |
| Itraconazole (SPORANOX ®)[5] | 14 | 54 |
| Luliconazole[6] | 14.9 | 45.4 |
| Terbinafine (P3058)[7] | 5.7 | 20.4 |

[1]Prescribing information Penlac ® Nail Lacquer (ciclopirox) 8%, (www.fda.gov)
[2]Prescribing information JUBLIA ® (efinaconazole) topical solution 10%, (www.fda.gov)
[3]Prescribing information KERYDIN ® (tavaborole) topical solution 8%, (www.fda.gov)
[4]Prescribing information LAMISIL ® (terbinafine hydrochloride) 250 mg, (www.fda.gov)
[5]Prescribing information SPORANOX ® (itraconazole) capsules, (www.fda.gov)
[6]Watanabe, S et al. (2017), J. Dermatology 44: 753-759
[7]EudraCT study 2015-000561-31, (www.clinicaltrialsregister.eu)

A graph showing the cure rates achieved in this study compared to the published results for other treatments shown in Table 2 is provided in FIG. 1. The graph shows that the level of complete cure achieved in this study was surprisingly low and not consistent with the expected relationship between mycological cure and complete cure seen for other treatments.

It was believed that the low complete cure rate may be attributed to excessive hydration of the nail occurring during treatment causing whitening discoloration of the nail and confounding assessment of complete cure. This discoloration and whitening was observed in both the treatment and vehicle control groups, suggesting that it is likely to be caused by the excipients in the composition. It was also noted that the discoloration/whitening of the nails improved between cessation of treatment at week 48 and assessment at week 52, suggesting that the appearance of the nail improves as the level of hydration decreases.

As can be seen from Table 3, high levels of mycological cure in the treatment group were also observed during earlier stages of the treatment regimen, suggesting that it is not necessary to apply the composition daily for the full period of treatment in order to achieve a high level of mycological cure. For comparison, treatment with oral terbinafine achieves around a 15% mycological cure rate after 12 weeks, around a 40% mycological cure rate at 24 weeks and around a 70% mycological cure rate at week 48/52 (Evans E. G. et al., BMJ, 1999, Apr. 17; 318 (7190): 1031-5; https://www.accessdata.fda.gov/drugsatfdadocs/label/2012/020539s021lbl.pdf).

TABLE 3

| | | Treatment group (n = 246) | Control group (n = 119) |
|---|---|---|---|
| Week 12 | Proportion | 37.4% | 11.8% |
| | (95% CI) | (31.3%, 43.8%) | (6.6%, 19.0%) |
| Week 24 | Proportion | 54.9% | 21.8% |
| | (95% CI) | (48.4%, 61.2%) | (14.8%, 30.4%) |
| Week 36 | Proportion | 60.2% | 22.7% |
| | (95% CI) | (53.7%, 66.3% | (15.5%, 31.3%) |
| Week 48 | Proportion | 64.6% | 25.2% |
| | (95% CI) | (58.3%, 70.6%) | (17.7%, 34.0%) |
| Week 52 | Proportion | 69.9% | 27.7% |
| | (95% CI) | (63.8%, 75.6%) | (19.9%, 36.7%) |

Example 2

Stable Compositions

The following compositions contain appropriate pharmaceutically acceptable excipients and have been found to form stable solutions of the active allylamine antifungal compound (terbinafine). Percentages refer to percentage by weight (w/w).

Composition 1

| | |
|---|---|
| Propylene glycol | 40% |
| Ethanol | 30% |
| Urea | 9% |
| Lactic acid | 9.9% |
| Terbinafine hydrochloride | 10% |
| Sodium hydroxide (10M) | 1% |
| Disodium EDTA | 0.1% |

Composition 2a

| | |
|---|---|
| Isopropylalcohol | 20% |
| Propylene glycol | 47.5% |
| Urea | 10% |
| Lactic acid | 5% |
| Ethanol | 5% |
| Sodium hydroxide (10M) | 2% |
| Terbinafine hydrochloride | 10% |
| Sodium phosphonate | 0.5% |

Composition 2b

| | |
|---|---|
| Isopropylalcohol | 20% |
| Propylene glycol | 48.5% |
| Urea | 10% |
| Lactic acid | 5% |
| Ethanol | 5% |
| Sodium hydroxide (5M) | 1% |
| Terbinafine hydrochloride | 10% |
| Sodium phosphonate | 0.5% |

Composition 3a

| | |
|---|---|
| Propylene glycol | 40% |
| Ethanol | 24.95% |
| Urea | 20% |
| Lactic acid | 5% |
| Glycerol | 5% |
| Terbinafine hydrochloride | 5% |
| Disodium EDTA | 0.05% |

Composition 3b

| | |
|---|---|
| Propylene glycol | 40% |
| Ethanol | 24.2% |
| Urea | 20% |
| Lactic acid | 5% |
| Glycerol | 5% |
| Terbinafine hydrochloride | 5% |
| Sodium hydroxide (5M) | 0.75% |
| Disodium EDTA | 0.05% |

Composition 4

| | |
|---|---|
| Propylene glycol | 30% |
| Ethanol | 30% |
| Urea | 10% |
| Lactic acid | 9.9% |
| Ethyl lactate | 10% |
| Terbinafine hydrochloride | 10% |

Composition 5

| | |
|---|---|
| Propylene glycol | 20% |
| Isopropylalcohol | 10% |
| Isopropyl lactate | 20% |
| Terbinafine hydrochloride | 5% |
| Ethanol | 15% |
| Urea | 20% |
| Lactic acid | 10% |

Composition 6

| | |
|---|---|
| 1,3-propylene glycol | 5% |
| Propylene glycol | 30% |

-continued

| | |
|---|---|
| Ethanol | 20% |
| Terbinafine hydrochloride | 10% |
| Urea | 15% |
| Lactic acid | 10% |
| Ethyl lactate | 10% |

Composition 7

| | |
|---|---|
| Ethyl lactate | 20% |
| Lactic acid | 10% |
| Urea | 10% |
| Propylene glycol | 25% |
| Terbinafine hydrochloride | 10% |
| Pentanoic acid | 5% |
| Ethanol | 20% |

Composition 8a

| | |
|---|---|
| Citric acid | 2% |
| Lactic acid | 8% |
| Ethyl lactate | 10% |
| Ethanol | 30% |
| Propylene glycol | 30% |
| Terbinafine hydrochloride | 10% |
| Urea | 10% |

Composition 8b

| | |
|---|---|
| Citric acid | 2% |
| Lactic acid | 8% |
| Ethyl lactate | 10% |
| Ethanol | 30% |
| Propylene glycol | 29% |
| Terbinafine hydrochloride | 10% |
| Urea | 10% |
| Sodium hydroxide (5M) | 1% |

Composition 9

| | |
|---|---|
| Propylene glycol | 39% |
| Ethanol | 24% |
| Ethyl lactate | 5% |
| Lactic Acid | 10% |
| Urea | 10% |
| Terbinafine hydrochloride | 10% |
| Polysorbate 80 | 1% |
| Sodium hydroxide (5M) | 1% |

The following compositions also contain pharmaceutically acceptable components in accordance with the invention.

Composition 10

| | |
|---|---|
| Propylene glycol | 30% |
| Butyl acetate | 35% |
| Urea | 10% |
| Lactic acid | 9.9% |
| Terbinafine hydrochloride | 10% |
| Polysorbate 80 | 5% |
| Calcium EDTA | 0.1% |

Composition 11

| | |
|---|---|
| Propylene glycol | 30% |
| Propyl acetate | 30% |
| Ethyl acetate | 5% |
| Urea | 10% |
| Lactic acid | 9.9% |
| Terbinafine hydrochloride | 10% |
| Polysorbate 80 | 5% |
| Sodium EDTA | 0.1% |

Composition 12

| | |
|---|---|
| Ethylene glycol | 10% |
| Propylene glycol | 30% |
| Propyl acetate | 20% |
| Butyl acetate | 10% |
| Lactic Acid | 10% |
| Urea | 10% |
| Terbinafine hydrochloride | 10% |
| Polysorbate 60 | 5% |

Composition 13

| | |
|---|---|
| Propylene glycol | 55% |
| Propyl acetate | 10% |
| Butyl acetate | 5% |
| Lactic Acid | 10% |
| Urea | 5% |
| Terbinafine hydrochloride | 10% |
| Lecithin | 2.5% |
| Polysorbate 80 | 2.5% |

Composition 14

| | |
|---|---|
| Propylene glycol | 50% |
| Propyl acetate | 5% |
| Butyl acetate | 5% |
| Lactic Acid | 10% |
| Urea | 10% |
| Terbinafine hydrochloride | 10% |
| Monoglycerides | 5% |
| Polysorbate 80 | 5% |

Example 3

Clinical Study

The composition used in the clinical study described in Comparative Example 1 is assessed for efficacy and safety as a topical treatment of mild to moderate distal subungual onychomycosis (DSO) in a multi-centre, double-blind, randomized, vehicle-controlled clinical trial.

The subjects are split into two treatment groups. The first group receives the terbinafine composition and the second group receives the vehicle control (the composition without the active ingredient terbinafine). The treatments are applied to all affected fingernails and toenails, but fingernails are not assessed for efficacy. A target toenail (large toenail) for the assessment of efficacy is selected for each subject and followed throughout the study.

For inclusion in the study, subjects need to be between 12 and 75 years of age and have DSO of at least one of the great toenail(s) affecting 20% to 60% of the target nail (evaluated by a central blind assessor on the basis standardized photo documentation, and diagnosis of DSO confirmed through a positive culture of dermatophytes or culture and KOH microscopy).

The treatments are applied topically to cover all affected toenails and fingernails with a thin layer and under the free edge of the nails and to the skin of the lateral and proximal nail folds, with a frequency according to one of the following 48-week treatment regimens:

(i) once daily for a period of 8 weeks, then once weekly for a period of 40 weeks;

(ii) once daily for a period of 10 weeks, then once weekly for a period of 38 weeks;

(iii) once daily for a period of 12 weeks, then once weekly for a period of 36 weeks.

The compositions are applied during the evening the feet and allowed to dry for approximately 5 minutes after application. The first application of the compositions is performed on site and under supervision. Any nails other than the target toenail that were considered by the investigator to be clinically cured before week 48.

The treated nails are assessed at 12-week intervals (weeks 12, 24, 36 and 48) and then four weeks after cessation of treatment (week 52) and the levels of mycological cure (negative culture of dermatophytes and KOH microscopy) and complete cure (0% clinical disease involvement and mycological cure) at each stage are determined.

After cessation of treatment, the treatment regimens achieve a comparable level of mycological cure to the level achieved in the study described in Comparative Example 1 but higher levels of complete cure that are more consistent with the correlation between mycological cure and complete cure observed for other approved treatments (as shown in FIG. 1).

Example 4

Nail Penetration Assay

Compositions 2b, 3b, 6, 8b and 9 from Example 2 and the composition used in the clinical trial described in Comparative Example 1 (reference formulation) were tested in an in vitro penetration assay using a Franz cell fitted with a bovine hoof membrane, which is a model for human nails (Mertin, D. Lippold, B. C. (1997) "In vitro permeability of the human nail and of a keratin membrane from bovine hooves: prediction of the penetration rate of antimycotics through the nail plate and their efficacy" J. Pharm. Pharmacol, 49:9, 866-72).

A controlled amount of each test composition (approximately 200 mg) was applied to the top of a clean and hydrated 100 μm bovine hoof membrane. The membranes are mounted into a diffusion (Franz) cell and contacted with a buffered receptor solution. The compositions penetrate through the membrane and into a receptor solution and the concentration of the active ingredient (terbinafine) in the receptor solution was measured. The receptor solution was sampled at regular time intervals to determine the penetration of the ingredients of the compositions through the hoof membrane over time. The receptor solution was initially sampled at regular time intervals to determine the penetration of the terbinafine through the hoof membrane over time. The results shown in the table below after 6 hr, at which time the flux was found to be stable and linear with time.

The level of flux of terbinafine through the bovine hoof membrane for the compositions of Example 2 compared to the reference formulation are shown in the table below. The compositions all achieved high levels of flux of the active ingredient through the hoof membrane that were similar to the flux of the active ingredient for the reference composition (composition of Comparative Example 1).

| Test Composition | Reference formulation | Cumulative amount for test formulation (μg/cm$^2$) | Cumulative amount for reference formulation (μg/cm$^2$) | % compared to reference formulation |
|---|---|---|---|---|
| Composition 2b | 10% terbinafine | 137.8 ± 10.9 | 226.0 ± 19.0 | 61% |
| Composition 6 | 10% terbinafine | 468.1 ± 257.1 | 210.8 ± 16.3 | 222% |
| Composition 8b | 10% terbinafine | 180.9 ± 6.0 | 165.7 ± 3.7 | 109% |
| Composition 9 | 10% terbinafine | 337.3 ± 51.2 | 295.1 ± 35.0 | 114% |
| Composition 3b | 5% terbinafine[1] | 265.4 ± 15.4 | 223.2 ± 14.3 | 119% |

[1]Modified reference composition containing terbinafine hydrochloride (5% w/w), propane-1,2-diol (64.7% w/w), lactic acid (9% w/w), EDTA(0.05% w/w), urea (18% w/w) and aqueous 10M sodium hydroxide solution.

The invention claimed is:

1. A method of treatment of onychomycosis of the nail, which method comprises the steps of:

(a) a loading phase that comprises once daily topical application to the nail of a pharmaceutically-acceptable composition comprising terbinafine, or a pharmaceutically acceptable salt thereof, for a period of about six months; followed by (b) a maintenance phase that comprises topical application to the nail of a pharmaceutically-acceptable composition comprising terbinafine, or a pharmaceutically acceptable salt thereof, at a frequency of no more than once a week, for a period of about six months, wherein the pharmaceutically-acceptable composition comprising terbinafine or a pharmaceutically acceptable salt thereof further comprises a non-aqueous solvent system that includes one or more excipients;

wherein the terbinafine or pharmaceutically acceptable salt thereof is present in the pharmaceutically-acceptable composition in an amount of from about 8% w/w to about 12% w/w; and wherein the one or more excipients are selected from the group:

(i) a monoalkyl alcohol selected from the group consisting of ethylene glycol, propylene glycol, butanediol, pentanediol, hexanediol, and mixtures thereof;

(ii) an organic acid selected from the group consisting of hydroxybutyric acid, a hydroxypropionic acid glycolic acid, citric acid, malic acid, tartaric acid, and mixtures thereof;

(iii) an aminoacetic acid sequestering agent; and (iv) a urea-based component selected from the group consisting of urea and urea peroxide.

2. The method of treatment as claimed in claim 1, wherein the loading phase is for a period of about 26 weeks.

3. The method of treatment as claimed in claim 1, wherein the loading phase is for a period of about 24 weeks.

4. The method of treatment as claimed in claim 1, wherein the maintenance phase is for a period of about 24 weeks.

5. The method of treatment as claimed in claim 1, wherein the maintenance phase is for a period of about 26 weeks.

6. The method of treatment as claimed in claim 1, wherein:

(a) the loading phase is for a period of about 24 or about 26 weeks; and (b) the maintenance phase is for a period of about 24 or about 26 weeks.

7. The method of treatment as claimed in claim 1, wherein the one or more excipients comprise:

(i) one of said monoalkyl alcohols;

(ii) one of said organic acids;

(iii) one er more aminoacetic acid sequestering-agent; and (iv) one of said urea-based components.

8. The method of treatment as claimed in claim 1 , wherein the one or more excipients are propylene glycol, a hydroxypropionic acid that is lactic acid, EDTA and urea.

* * * * *